United States Patent
Leone et al.

(10) Patent No.: US 10,624,764 B2
(45) Date of Patent: Apr. 21, 2020

(54) SYSTEM AND METHOD FOR THE REGISTRATION OF AN ANATOMICAL FEATURE

(71) Applicant: ORTHOSOFT, INC., Montreal (CA)

(72) Inventors: Yvan Leone, Montreal (CA); Mathieu Chevrier, Roxboro (CA); Myriam Valin, Laval (CA); Bruno Falardeau, Verdun (CA); Benoit Pelletier, Laval (CA); Karine Duval, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 440 days.

(21) Appl. No.: 15/361,928

(22) Filed: Nov. 28, 2016

(65) Prior Publication Data
US 2017/0151018 A1 Jun. 1, 2017

Related U.S. Application Data

(60) Provisional application No. 62/260,296, filed on Nov. 26, 2015.

(51) Int. Cl.
*A61F 2/46* (2006.01)
*A61B 34/20* (2016.01)
(Continued)

(52) U.S. Cl.
CPC ........ *A61F 2/4657* (2013.01); *A61B 17/1746* (2013.01); *A61B 2034/105* (2016.02); *A61F 2002/4658* (2013.01)

(58) Field of Classification Search
CPC ................ A61B 17/1764; A61B 34/20; A61B 2034/2046; A61B 2034/2048;
(Continued)

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.

(Continued)

*Primary Examiner* — Eric S Gibson
(74) *Attorney, Agent, or Firm* — Norton Rose Fulbright Canada LLP

(57) ABSTRACT

A computer-assisted surgery (CAS) system for navigating a surface of an anatomical feature in a coordinate system comprises an apparatus for obtaining points of a surface of an anatomical feature including a base adapted to be secured to the anatomical feature, a spherical joint supported by the base, the spherical joint having a ball member rotatable in at least two rotational degrees of freedom relative to the base and having a center of rotation fixed relative to the base, a distance-measurement device connected to the ball member such that a distance-measurement axis of the distance-measurement device passes through said center of rotation of the ball member. An inertial sensor unit produces signals representative of the orientation of the distance-measurement device. A CAS processor receives the signal from the at least one inertial sensor unit and outputs orientation data relating at least an object relative to the surface of the anatomical feature using the model of the surface in the (Continued)

coordinate system and the signals from the at least one inertial sensor unit.

12 Claims, 7 Drawing Sheets

(51) Int. Cl.
*A61B 17/17* (2006.01)
*A61B 34/10* (2016.01)

(58) Field of Classification Search
CPC ..... A61B 2034/2059; A61B 2034/2068; A61F 2/4657; A61F 2002/4658
See application file for complete search history.

(56) References Cited

U.S. PATENT DOCUMENTS

| | | | |
|---|---|---|---|
| 5,490,854 A | 2/1996 | Fisher et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 6,327,491 B1 * | 12/2001 | Franklin | A61B 90/11 600/429 |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 9,539,112 B2 * | 1/2017 | Thornberry | A61F 2/4609 |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0010301 A1 * | 1/2005 | Disilvestro | A61B 5/076 623/18.12 |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 * | 5/2009 | Park | A61B 17/154 606/87 |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarksi et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |
| 2010/0023015 A1 | 1/2010 | Park | |
| 2010/0042105 A1 | 2/2010 | Park et al. | |
| 2010/0049195 A1 | 2/2010 | Park et al. | |
| 2010/0054572 A1 | 3/2010 | Tsougarakis et al. | |

(56) References Cited

U.S. PATENT DOCUMENTS

| | | |
|---|---|---|
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0191298 A1* | 7/2010 | Earl ............ A61B 17/155 606/86 R |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1* | 3/2011 | Angibaud ............ A61B 17/155 606/89 |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1* | 7/2011 | Meridew ............ A61B 17/151 606/80 |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1* | 12/2011 | Bono ............ A61B 17/1746 606/91 |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1* | 2/2012 | Roose ............ A61B 17/1746 606/96 |
| 2012/0041446 A1 | 2/2012 | Wong et al. |
| 2012/0065640 A1* | 3/2012 | Metzger ............ A61B 17/154 606/88 |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1* | 9/2012 | Kunz ............ A61B 17/1746 606/86 R |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2012/0323247 A1* | 12/2012 | Bettenga ............ A61F 2/46 606/91 |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |

(56) References Cited

U.S. PATENT DOCUMENTS

| | | | |
|---|---|---|---|
| 2013/0184713 A1* | 7/2013 | Bojarski | A61B 17/154 606/88 |
| 2013/0197870 A1 | 8/2013 | Steines et al. | |
| 2013/0211409 A1 | 8/2013 | Burdulis, Jr. et al. | |
| 2013/0211410 A1 | 8/2013 | Landes et al. | |
| 2013/0211531 A1 | 8/2013 | Steines et al. | |
| 2013/0245803 A1 | 9/2013 | Lang | |
| 2013/0253522 A1 | 9/2013 | Bojarski et al. | |
| 2013/0289570 A1 | 10/2013 | Chao | |
| 2013/0296874 A1 | 11/2013 | Chao | |
| 2013/0297031 A1 | 11/2013 | Hafez | |
| 2013/0317511 A1 | 11/2013 | Bojarski et al. | |
| 2013/0331850 A1 | 12/2013 | Bojarski et al. | |
| 2014/0005792 A1 | 1/2014 | Lang et al. | |
| 2014/0029814 A1 | 1/2014 | Fitz et al. | |
| 2014/0031826 A1 | 1/2014 | Bojarski et al. | |
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0236159 A1* | 8/2014 | Haider | A61B 17/1626 606/88 |
| 2014/0303631 A1* | 10/2014 | Thornberry | A61F 2/4609 606/91 |
| 2016/0015468 A1* | 1/2016 | Piron | A61B 5/6847 600/424 |
| 2016/0022374 A1* | 1/2016 | Haider | A61B 17/17 606/96 |
| 2016/0113720 A1* | 4/2016 | Lavallee | A61B 17/15 606/130 |
| 2017/0151018 A1* | 6/2017 | Leone | A61B 17/1746 |
| 2017/0360512 A1* | 12/2017 | Couture | A61B 34/10 |
| 2018/0085135 A1* | 3/2018 | Singh | A61B 17/1707 |
| 2018/0132949 A1* | 5/2018 | Merette | G06T 11/206 |
| 2018/0177612 A1* | 6/2018 | Trabish | A61F 2/4684 |
| 2018/0280037 A1* | 10/2018 | Dassonville | A61B 5/1072 |
| 2018/0280092 A1* | 10/2018 | Van Beek | A61B 90/39 |
| 2018/0311011 A1* | 11/2018 | Van Beek | A61B 90/96 |
| 2019/0000372 A1* | 1/2019 | Gullotti | A61B 17/7035 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |

(56) References Cited

FOREIGN PATENT DOCUMENTS

| | | | |
|---|---|---|---|
| EP | 2509539 | A2 | 10/2012 |
| EP | 2512381 | A2 | 10/2012 |
| EP | 2324799 | A3 | 1/2013 |
| EP | 2419035 | A4 | 1/2013 |
| EP | 2445451 | A4 | 3/2013 |
| EP | 2403434 | A4 | 4/2013 |
| EP | 2591756 | A1 | 5/2013 |
| EP | 2496183 | A4 | 12/2013 |
| EP | 2512381 | A4 | 12/2013 |
| EP | 2649951 | A2 | 12/2013 |
| EP | 2649951 | A3 | 12/2013 |
| EP | 2671520 | A3 | 12/2013 |
| EP | 2671521 | A3 | 12/2013 |
| EP | 2671522 | A3 | 12/2013 |
| EP | 2114312 | B1 | 1/2014 |
| EP | 2710967 | A2 | 3/2014 |
| GB | 2484042 | A | 3/2012 |
| GB | 2489884 | A | 10/2012 |
| GB | 201213674 | | 10/2012 |
| GB | 2484042 | B | 3/2014 |
| HK | 1059882 | A1 | 8/2011 |
| HK | 1072710 | A1 | 8/2011 |
| HK | 1087324 | A1 | 11/2011 |
| HK | 1104776 | A1 | 11/2011 |
| JP | 2006510403 | A | 3/2006 |
| JP | 2007514470 | A | 6/2007 |
| JP | 2011519713 | A | 7/2011 |
| JP | 2011224384 | A | 11/2011 |
| JP | 2012091033 | A | 5/2012 |
| JP | 2012176318 | A | 9/2012 |
| JP | 5053515 | B2 | 10/2012 |
| JP | 2012187415 | A | 10/2012 |
| JP | 2012523897 | A | 10/2012 |
| JP | 5074036 | B2 | 11/2012 |
| JP | 2012531265 | A | 12/2012 |
| JP | 2013503007 | A | 1/2013 |
| JP | 5148284 | B2 | 2/2013 |
| JP | 5198069 | B2 | 5/2013 |
| JP | 2014000425 | A | 1/2014 |
| KR | 20050072500 | A | 7/2005 |
| KR | 20050084024 | A | 8/2005 |
| KR | 20120090997 | A | 8/2012 |
| KR | 20120102576 | A | 9/2012 |
| MX | 2012007140 | A | 1/2013 |
| NZ | 597261 | A | 11/2013 |
| SG | 173840 | A1 | 9/2011 |
| SG | 175229 | A1 | 11/2011 |
| SG | 176833 | A1 | 1/2012 |
| SG | 178836 | A1 | 4/2012 |
| SG | 193484 | A1 | 10/2013 |
| TW | 200509870 | A | 3/2005 |
| TW | 1231755 | B | 5/2005 |
| TW | 200800123 | A | 1/2008 |
| TW | 1330075 | B | 9/2010 |
| WO | 2004049981 | A3 | 6/2004 |
| WO | 2004051301 | A3 | 6/2004 |
| WO | 2005051239 | A1 | 6/2005 |
| WO | 2005051240 | A1 | 6/2005 |
| WO | 2006058057 | A2 | 6/2006 |
| WO | 2006060795 | A1 | 6/2006 |
| WO | 2006058057 | A8 | 7/2006 |
| WO | 2007041375 | A2 | 4/2007 |
| WO | 2007062103 | A1 | 5/2007 |
| WO | 2007092841 | A2 | 8/2007 |
| WO | 2007109641 | A2 | 9/2007 |
| WO | 2007092841 | A3 | 11/2007 |
| WO | 2007109641 | A3 | 12/2007 |
| WO | 2008101090 | A2 | 8/2008 |
| WO | 2008112996 | A1 | 9/2008 |
| WO | 2008101090 | A3 | 11/2008 |
| WO | 2008157412 | A2 | 12/2008 |
| WO | 2007041375 | A3 | 4/2009 |
| WO | 2008157412 | A3 | 4/2009 |
| WO | 2009111626 | A2 | 9/2009 |
| WO | 2009111639 | A1 | 9/2009 |
| WO | 2009111656 | A1 | 9/2009 |
| WO | 2009140294 | A1 | 11/2009 |
| WO | 2009111626 | A3 | 1/2010 |
| WO | 2010099231 | A2 | 9/2010 |
| WO | 2010099353 | A1 | 9/2010 |
| WO | 2010121147 | A1 | 10/2010 |
| WO | 2010099231 | A3 | 11/2010 |
| WO | 2011028624 | A1 | 3/2011 |
| WO | 2011056995 | A2 | 5/2011 |
| WO | 2011072235 | A2 | 6/2011 |
| WO | 2011075697 | A2 | 6/2011 |
| WO | 2011056995 | A3 | 9/2011 |
| WO | 2011075697 | A3 | 10/2011 |
| WO | 2011072235 | A3 | 12/2011 |
| WO | 2012112694 | A1 | 8/2012 |
| WO | 2012112694 | A2 | 8/2012 |
| WO | 2012112698 | A2 | 8/2012 |
| WO | 2012112701 | A2 | 8/2012 |
| WO | 2012112702 | A2 | 8/2012 |
| WO | 2012112694 | A3 | 1/2013 |
| WO | 2012112701 | A3 | 1/2013 |
| WO | 2012112702 | A3 | 1/2013 |
| WO | 2013020026 | A1 | 2/2013 |
| WO | 2013025814 | A1 | 2/2013 |
| WO | 2012112698 | A3 | 3/2013 |
| WO | 2013056036 | A1 | 4/2013 |
| WO | 2013119790 | A1 | 8/2013 |
| WO | 2013119865 | A1 | 8/2013 |
| WO | 2013131066 | A1 | 9/2013 |
| WO | 2013152341 | A1 | 10/2013 |
| WO | 2013155500 | A1 | 10/2013 |
| WO | 2013155501 | A1 | 10/2013 |
| WO | 2014008444 | A1 | 1/2014 |
| WO | 2014035991 | A1 | 3/2014 |
| WO | 2014047514 | A1 | 3/2014 |

OTHER PUBLICATIONS

Hofmann et al, "Natural-Knee II System", Intermedics Orthopedics, Austin, TX, 1995.
https://www.youtube.com/watch?v=1iGfnrRyWTA.

* cited by examiner

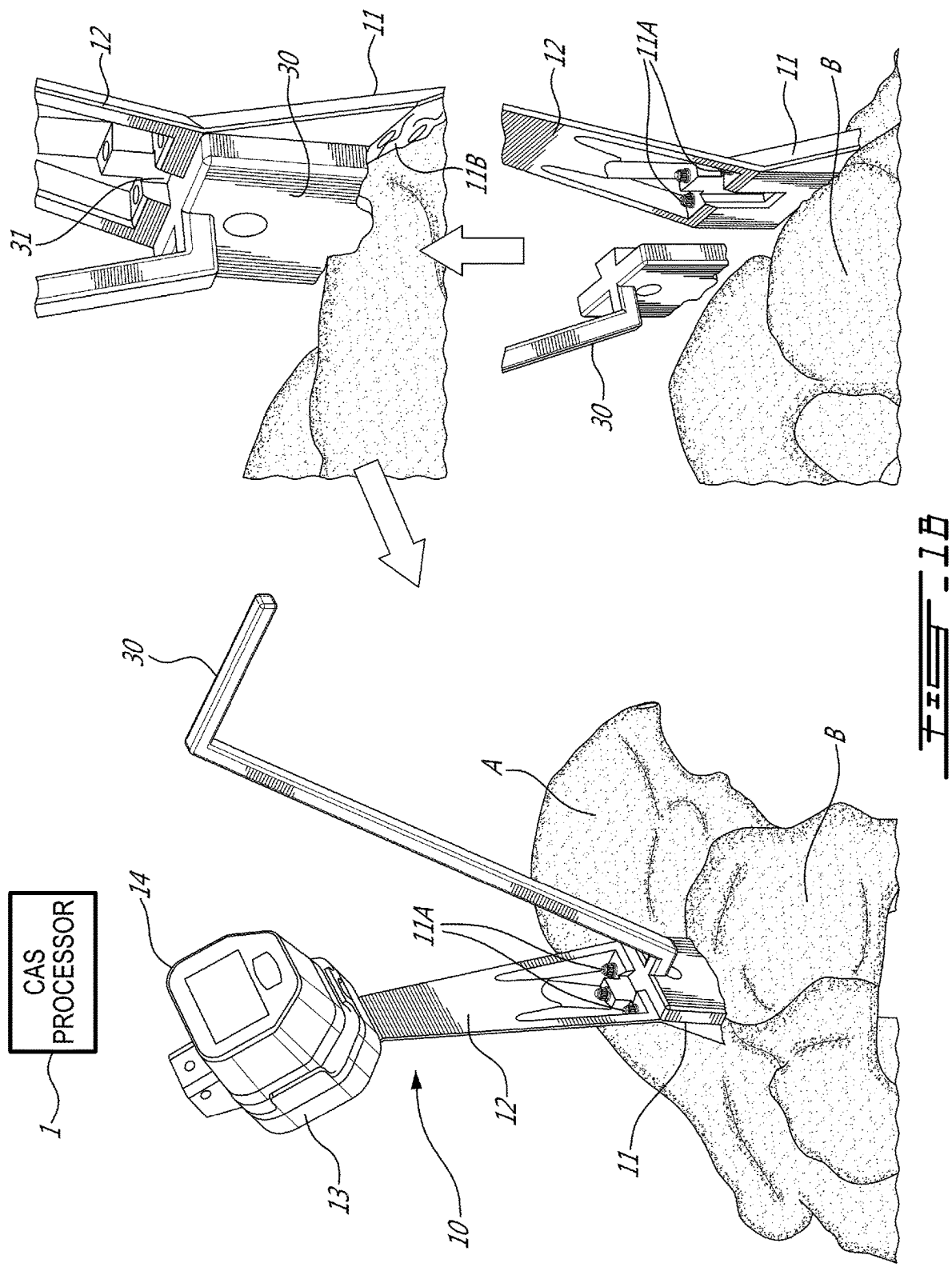

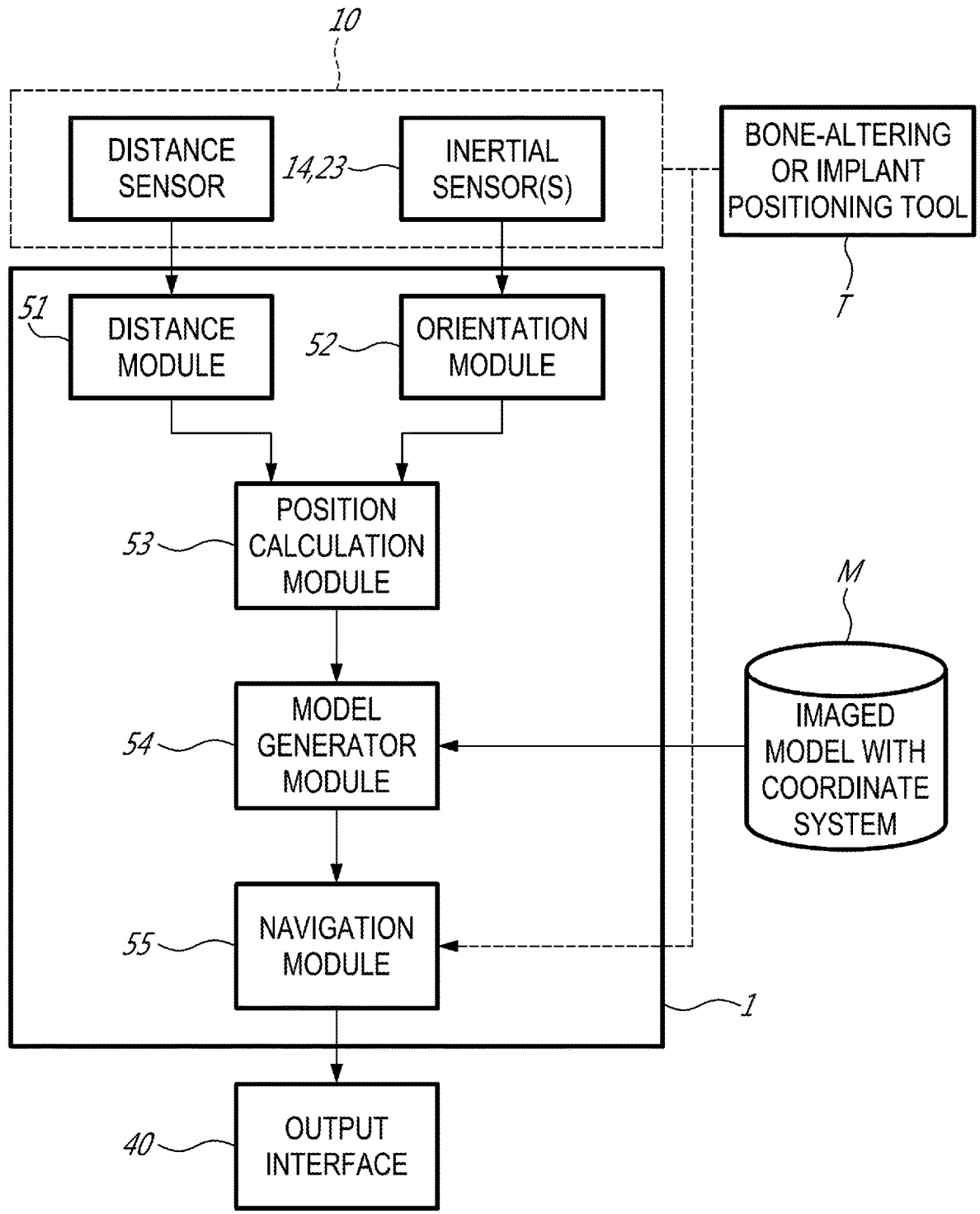

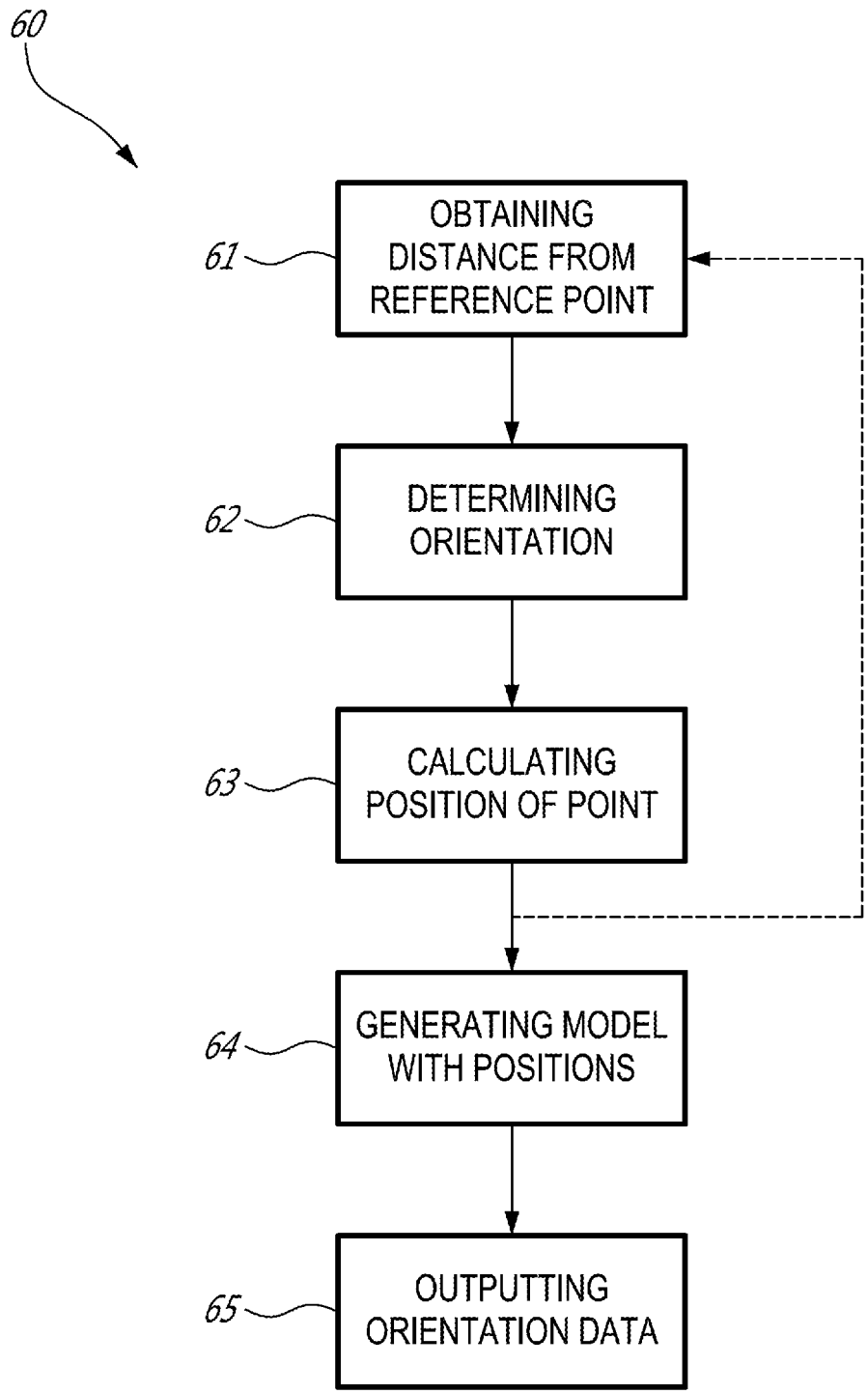

US 10,624,764 B2

SYSTEM AND METHOD FOR THE REGISTRATION OF AN ANATOMICAL FEATURE

CROSS-REFERENCE TO RELATED APPLICATION

The present application claims priority of U.S. Patent Application No. 62/260,296, filed on Nov. 26, 2015 and incorporated herein by reference.

TECHNICAL FIELD

The present application relates to computer-assisted surgery using inertial sensors and more particularly to referencing inertial sensors relative to a bone, for subsequent alterations to the bone.

BACKGROUND OF THE ART

In arthroplasty, a bone is altered to subsequently receive thereon an implant. For example, in hip arthroplasty, the acetabular cup implant is received in the reamed acetabulum and serves as a receptacle for a femoral head or femoral head implant. Accordingly, tools such as a reamer and a cup impactor are used in the procedure.

One of the challenges in such procedures is to provide an adequate orientation to the tool or implant relative to the bone. An inaccurate orientation, for instance in the case of an acetabular cup implant, may result in a loss of movements, improper gait, and/or premature wear of implant components. For example, the acetabular cup is typically positioned in the reamed acetabulum by way of an impactor. The impactor has a stem at an end of which is the acetabular cup. The stem is handled by an operator that impacts the free end so as to drive the acetabular cup into the acetabulum. It is however important that the operator holds the stem of the impactor in a precise three-dimensional orientation so as to ensure the adequate orientation of the acetabular cup, in terms of inclination and anteversion. Accordingly, the knowledge of the initial position and orientation of the bone relative to an inertial sensor unit can contribute to subsequent steps of altering the bone and positioning an implant thereon.

Computer-assisted surgery has been developed in order to help operators in positioning and orienting implants to a desired orientation. Among the various tracking technologies used in computer-assisted surgery, optical navigation, C-arm validation and manual reference guides have been used. The optical navigation requires the use of a navigation system, which adds operative time. Moreover, it is bound to line-of-sight constraints which hamper the normal surgical flow. C-arm validation requires the use of bulky equipment and the validation is not cost-effective, yet does not provide a quantitative assessment of the cup positioning once done, and is generally used post-operatively as opposed to intra-operatively. Finally, manual jigs, such as an A-frame, do not account for the position of the patient on the operative table. Accordingly, inertial sensors are used for their cost-effectiveness and the valuable information they provide.

SUMMARY

Therefore, in accordance with a first embodiment of the present disclosure, there is provided an apparatus for obtaining points of a surface of an anatomical feature comprising: a base adapted to be secured to an anatomical feature; a spherical joint supported by the base, the spherical joint having a ball member rotatable in at least two rotational degrees of freedom relative to the base and having a center of rotation fixed relative to the base; a distance-measurement device connected to the ball member such that a distance-measurement axis of the distance-measurement device passes through said center of rotation of the ball member, the distance-measurement device configured for providing a distance of any point of the surface intersecting the distance-measurement axis; and at least one receptacle configured to receive an inertial sensor unit for determining an orientation of the distance-measurement device; whereby a position of any point is obtained using said distance and an orientation of the distance-measurement device as connected to the ball member at a measurement of said point.

In accordance with a second embodiment of the present disclosure, there is provided a method for modelling a surface of an anatomical feature in computer-assisted surgery (CAS) in a coordinate system, comprising: obtaining a distance between a reference position and any point of the surface of the anatomical feature; determining, using at least one inertial sensor unit and one or more processors of a CAS system, an orientation of an axis passing through the reference position and said any point of the surface of the anatomical feature; calculating a position of said any point using the orientation of the axis and the distance for said any point; repeating the obtaining the distance, the determining the orientation and the calculating a position for a plurality of points on the anatomical feature, with the reference position being fixed throughout the repeating; generating, using the at least one inertial sensor unit and one or more processors of the CAS system, the model of the surface in the coordinate system using at least the position of the plurality of points; and outputting, using the at least one inertial sensor unit and one or more processors of the CAS system, orientation data relating at least an object relative to the surface of the anatomical feature using the model of the surface in the coordinate system.

In accordance with a third embodiment of the present disclosure, there is provided a computer-assisted surgery (CAS) system for navigating a surface of an anatomical feature in a coordinate system comprising: an apparatus for obtaining points of a surface of an anatomical feature including a base adapted to be secured to the anatomical feature, a spherical joint supported by the base, the spherical joint having a ball member rotatable in at least two rotational degrees of freedom relative to the base and having a center of rotation fixed relative to the base, a distance-measurement device connected to the ball member such that a distance-measurement axis of the distance-measurement device passes through said center of rotation of the ball member, the distance-measurement device for providing a distance of any point of the surface intersecting the distance-measurement axis, and at least one receptacle for receiving an inertial sensor unit; at least one inertial sensor unit received in the receptacle of the apparatus, the at least one inertial sensor unit producing signals representative of the orientation of the distance-measurement device; a CAS processor receiving the signal from the at least one inertial sensor unit and including a distance module for obtaining a distance between a reference position and a plurality of points of the surface of the anatomical feature, an orientation module for determining, using the signal from the at least one inertial sensor unit, an orientation of the distance-measurement axis for each of the plurality of points, a position calculator module for calculating a position of each of the plurality of points using the orientation of the distance-measurement axis, the distance for each of the plurality of points, and the reference position being common to each of the plurality of points, a model generating module for generating the model of the surface in the coordinate system using at least the position of the plurality of points and the signals from the at least one inertial sensor unit, and a navigation module for producing orientation data relating at least an object relative to the surface of the anatomical feature using the model of the surface in the coordinate system and the signals from the at least one inertial sensor unit; and an output for outputting the orientation data.

In accordance with a fourth embodiment of the present disclosure, there is provided a CAS processor for modelling a surface of an anatomical feature in computer-assisted surgery (CAS) in a coordinate system, comprising: a distance module for obtaining a distance between a reference position and a plurality of points of the surface of the anatomical feature; an orientation module for determining, using signals from at least one inertial sensor unit, an orientation of an axis passing through the reference position and the plurality of points of the surface of the anatomical feature, a position calculator module for calculating a position of said any point using the orientation of the axis and the distance for said any point, the reference position being common to each of the plurality of points, a model generating module for generating and outputting, using the signals from the at least one inertial sensor unit, the model of the surface in the coordinate system using at least the position of the plurality of points, and a navigation module for producing and outputting, using the signals from the at least one inertial sensor unit, orientation data relating at least an object relative to the surface of the anatomical feature using the model of the surface in the coordinate system.

DESCRIPTION OF THE DRAWINGS

FIG. 1B is a series of perspective views of the apparatus of the CAS system, with a tab handle assisting in the positioning of the apparatus on the pelvis;

FIG. 5 is a block diagram of a CAS processor for modelling a surface of an anatomical feature in computer-assisted surgery in a coordinate system; and FIG. 6 is a flow chart illustrating a method for modelling a surface of an anatomical feature in computer-assisted surgery in a coordinate system.

DETAILED DESCRIPTION

Figure 1A:
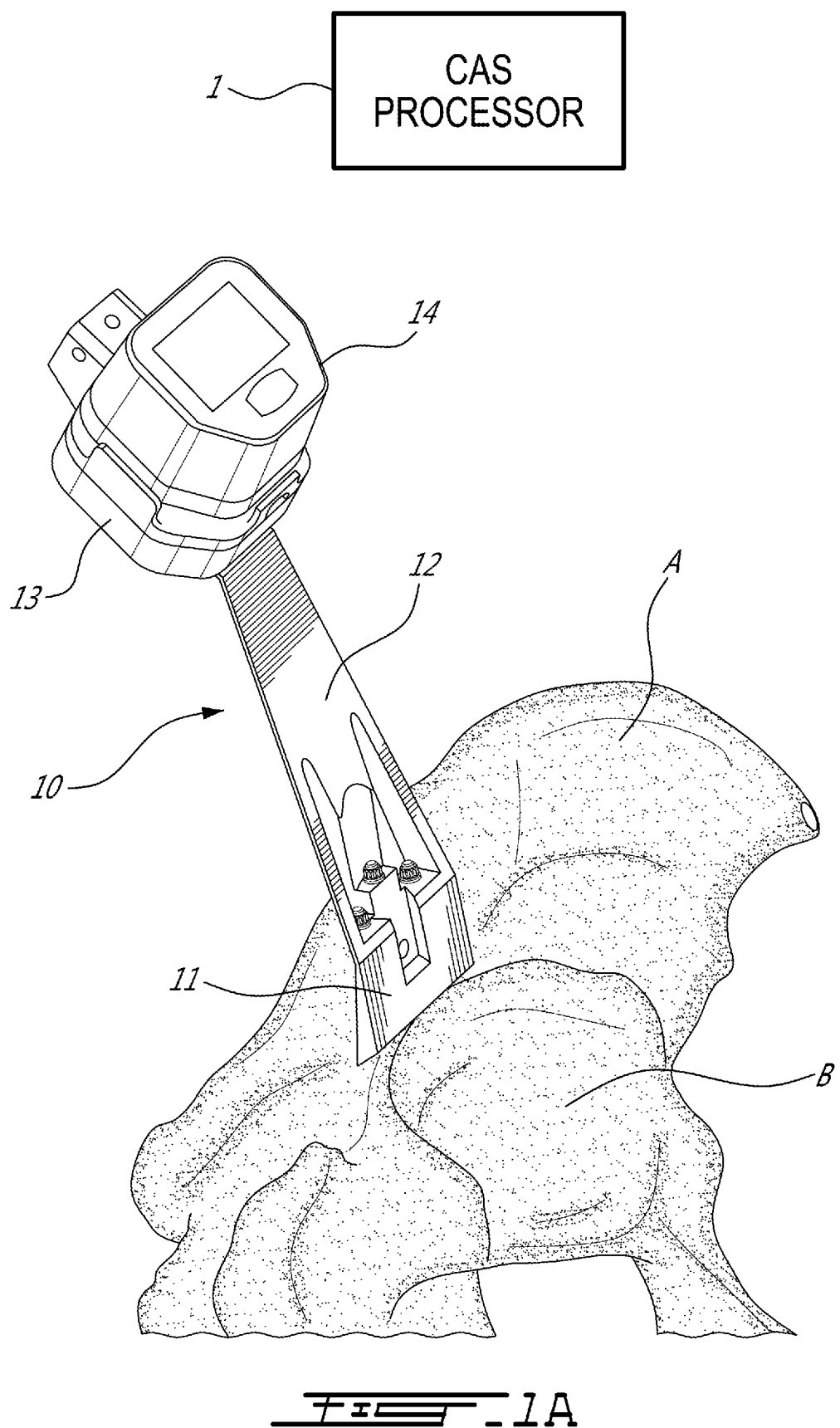
FIG. 1A is a perspective view of an apparatus of a CAS system on a pelvis.

Referring to the drawings, a method for referencing an inertial sensor unit relative to an anatomical feature in computer-assisted hip surgery is generally shown. Although the example provided herein relates to hip surgery, with the anatomical feature being the pelvis, other types of surgery may benefit from the method and instrumentation of the present disclosure. The purpose of method is to enable accurate navigation of instruments used in hip arthroplasty or like procedures using inertial sensors.

As an initial point, the bone may be modeled. The imaged model may be obtained and/or generated using imaging. The imaging may be done by any appropriate technology such as CT scanning (computerized tomography), fluoroscopy, or like radiography methods, providing suitable resolution of images. The model of the bone may include a surface geometry of its surface to be altered and other parts of the bone that are exposed. In particular, if applicable, a combination of radiography and magnetic resonance imagery (MRI) may provide a suitable resolution between bone and cartilage, useful to recognize the boundaries of cartilage relative to the bone. The bone modeling may comprise generating a 3D surface of the bone if the bone modeling is not directly performed by the imaging equipment, or if not complete. The model may alternatively be composed of a two-dimensional (2D) outline instead of a three-dimensional (3D) surface, as such a 2D outline may provide sufficient data to determine how a reference will be secured to a bone.

In the case of hip arthroplasty, the pelvis may be imaged as a whole, or key parts may be more detailed in a generic model. For example, if given bone landmarks will be used to facilitate navigation or as abutment surfaces, the model may feature additional resolution for such landmarks. In hip arthroplasty, an example would be the acetabulum and surroundings as the acetabulum receives the cup implant, and the iliac crest (e.g., anterior-superior iliac spine, ASIS) as they are landmarks often used to guide an operator in orienting tools (e.g., impactor). For example, the 3D images bone model may also include an orientation of the anatomical feature, such as a coordinate system. In the case of the pelvis, the coordinate system may include for example a medio-lateral axis passing through the antero-superior iliac spines (ASIS), and a cranial-caudal axis using the position of the pubic turbercle relative to the ASIS, among other possibilities, as determined using the images and added to the imaged bone model. The anterior-posterior axis would be obtained as normal to the plane including the medio-lateral axis and the cranial-caudal axis. Therefore, the orientation of the anatomical feature is a virtual orientation that may be part of the virtual 3D model of the surface.

Referring to FIG. 1A, a system for navigating instruments in computer-assisted hip surgery is shown, and is of the type used to implement the method, as will be detailed below. The system comprises a computer-assisted surgery (CAS) processing unit 1, shown as a stand-alone unit in FIG. 1A. It is however pointed out that the CAS processing unit 1 may be integrated into one or more inertial sensor units such as 14 and 23 described hereinafter, also known as pods, mounted to the various devices and instruments of the system 1, namely an apparatus 10 and a distance-measuring device 20.

The inertial sensor units incorporating the processing unit 1 may thus be equipped with user interfaces to provide the navigation data, whether it be in the form of LED displays, screens, numerical displays, etc. Alternatively, the inertial sensor units may be connected to a stand-alone CAS processing unit 1 that would include a screen or like monitor. The inertial sensor units may be known as micro-electro-mechanical sensors (MEMS) and may include one or more accelerometers, gyroscopes, inclinometers, magnetometers, among other possible inertial sensors. The inertial sensor units are of the type providing orientation data along 3 axes, hence tracking three rotational degrees of freedom of movement. The CAS processing unit 1 may comprise geometrical data for some of the devices and instruments. Accordingly, when an inertial sensor unit is mounted to one of the devices and instruments, the relation between the device/instrument and a coordinate system of the inertial sensor unit is known. For example, the relation is between an axis or a 3D coordinate system of the device/instrument and the coordinate system of the inertial sensor unit. Moreover, the inertial sensor units may be portable and detachable units, used with one device/instrument, and then transferred to another device/instrument, preserving in the process orientation data of a global coordinate system, using for example dead-reckoning tracking with readings from the inertial sensor unit(s). The navigation of instruments is intended to mean tracking at least some of the degrees of freedom of orientation in real-time or quasi-real time, such that the operator is provided with data calculated by computer assistance.

The apparatus 10 and the distance-measuring device 20 are provided to assist in defining a model of a surface of the bone, in a coordinate system, with the inertial sensor unit(s) of the apparatus 10 remaining active afterwards to track other tools relative to the bone. Other devices may be used to assist in the positioning of the apparatus 10 to the pelvis, such as a tab handle 30. Hence, other devices may be used subsequently to complete the surgical procedure, such as drills, impactors, reamers, guiding pins, etc.

Figure 2:
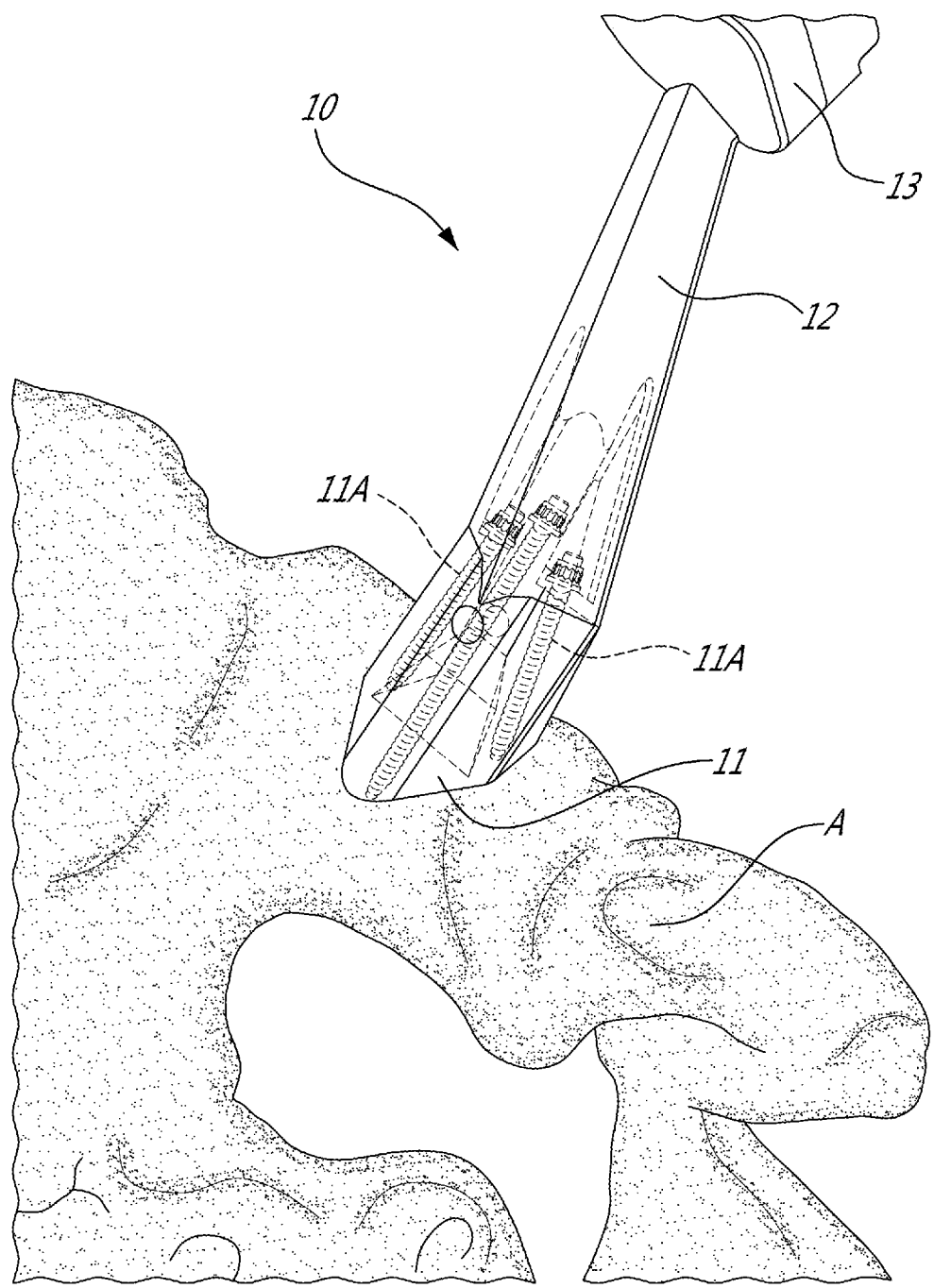
FIG. 2 is a perspective enlarged view showing a connection of the apparatus to the pelvis.

Referring to FIGS. 1A, 1B and 2, the apparatus 10 has a base 11 by which it is connected to a bone, such as the pelvis A featuring acetabulum B. For clarity, reference is made hereinafter to the case of hip surgery, as an example, even though the system and method may be applied to other bones. FIG. 1B illustrates the use of tab handle 30, releasably secured to the base 11 of the apparatus 10, to position same against the pelvis. The tab handle 30 may stabilize the apparatus 10 over the acetabulum rim, to position the apparatus 10 on bone surfaces adjacent to the rim. The tab handle 30 may be used to hold the apparatus 10 at the chosen location while inserting fasteners such as screws 11A, for instance by having a contact portion defined to abut against the pelvis, in such a way that the apparatus 10 and tab handle 30 concurrently grip the rim of the acetabulum. To assist in positioning the base 11 in a desired position against the anatomical feature, the base 11 may have a patient-specific surface, as is shown at 11B. The patient-specific surface 11B may be a contour-matching negative surface of the bone, defined using the 3D imaged bone model from pre-operative planning. However, the base 11 may also be without such surface. The tab handle 30 may be removed once the apparatus 10 is secured to the pelvis A, by the presence of a complementary tongue and groove joint shown as 31. As shown in FIG. 2, the base 11 may be secured to the bone by way of screws 11A, although other types of fasteners may be used as well. The base 11 has an upwardly projecting portion 12 which projects away from a remainder of the base 11, and has a receptacle 13 at its end, for receiving inertial sensor unit 14.

Figure 3:
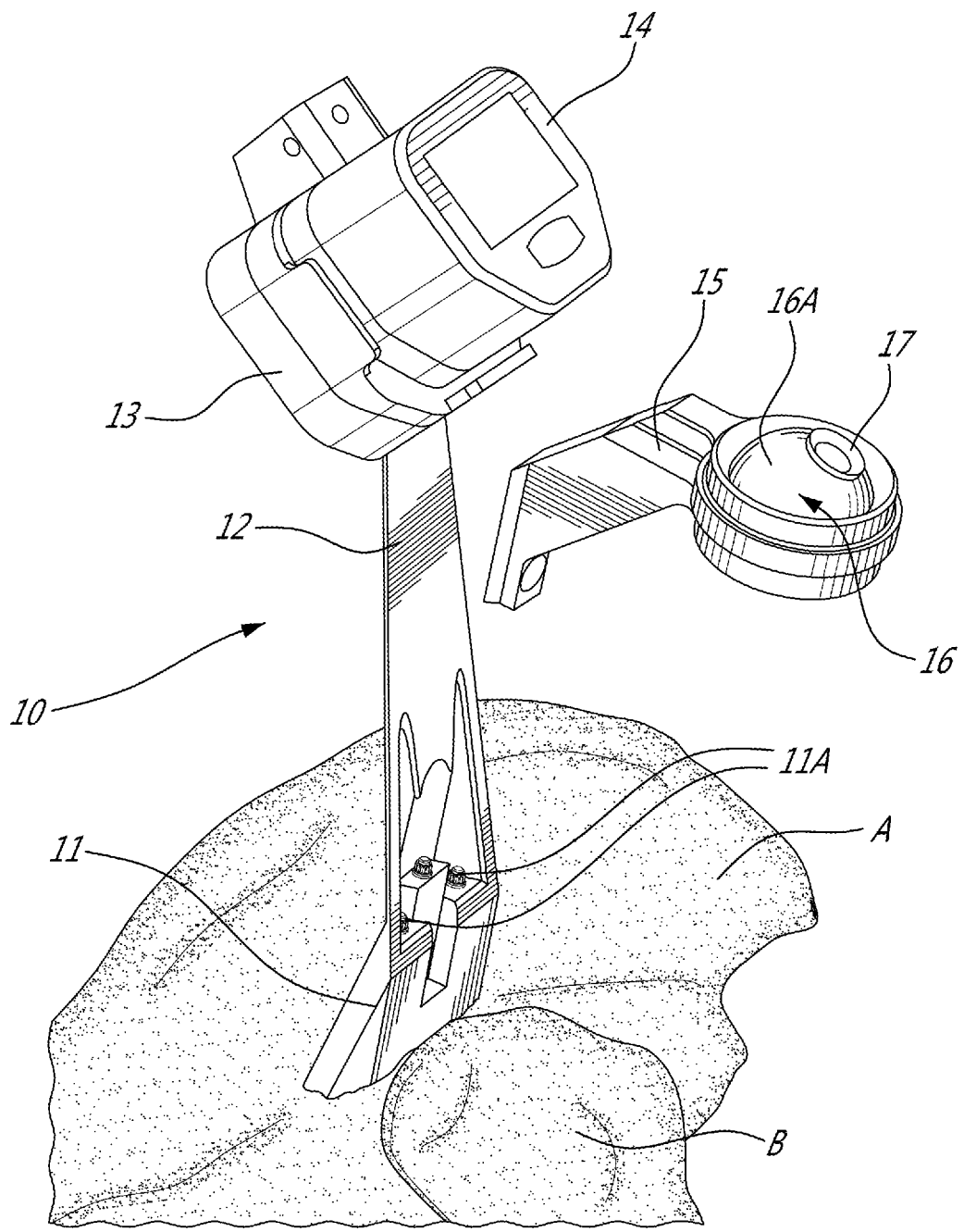
FIG. 3 is an assembly view of the apparatus of FIG. 1A, with a bracket.

Referring to FIG. 3, a bracket 15 may be releasably connectable to the base 11, or other part of the apparatus 10, and forms part of a spherical joint 16 at its end, with a central bore 17, such as a counterbore. In an embodiment, the geometric relation between the central bore 17 and the inertial sensor unit 14 is known, such that subsequent readings can be derived from this relation. The spherical joint 16 has a ball member 16A having its center of rotation fixed relative to the base 11.

Figure 4:
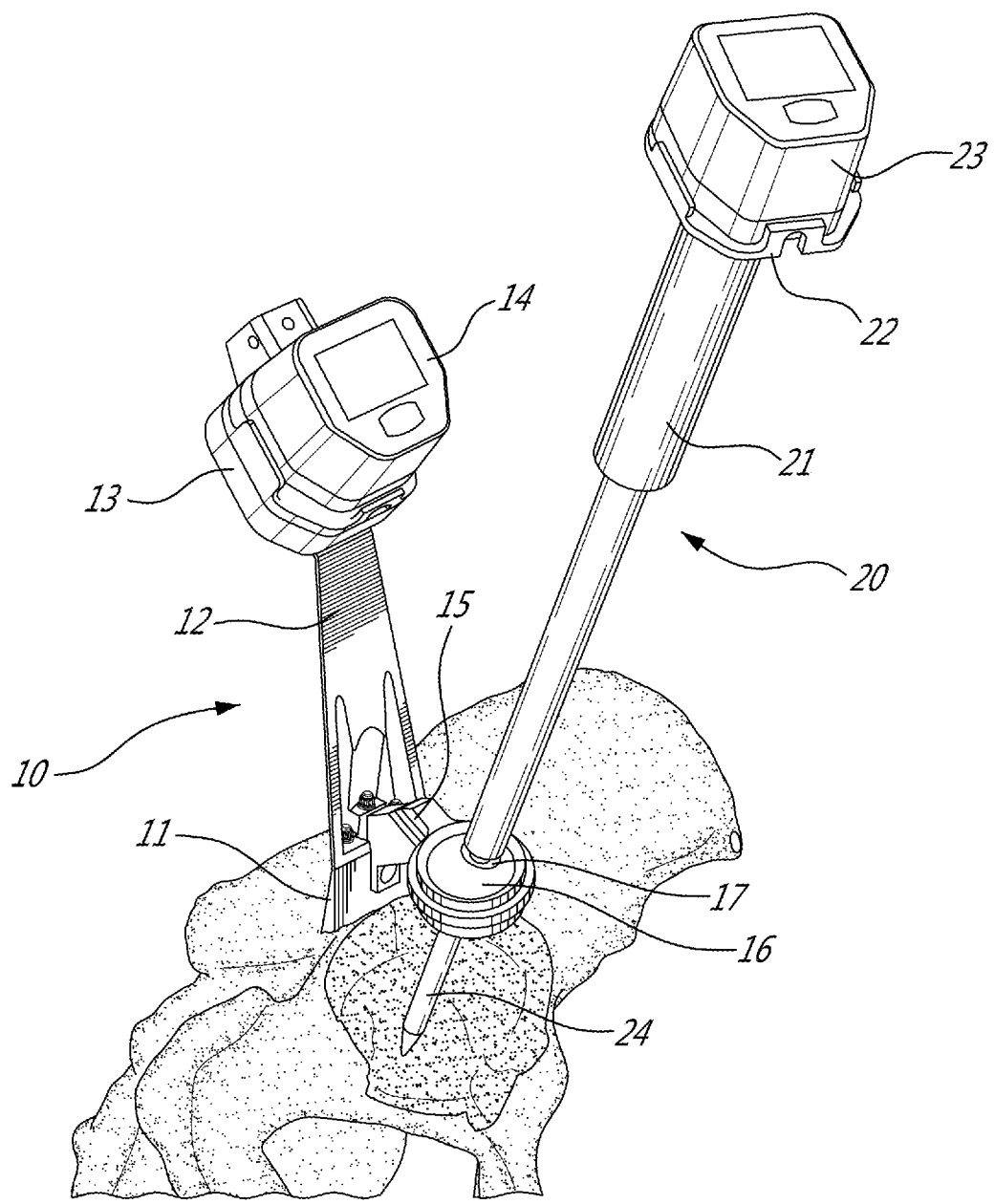
FIG. 4 is a perspective view showing a relation between the apparatus of FIG. 1A and a distance-measuring device.

Referring to FIG. 4, the spherical joint 16 is the interface of the base 11 with the distance-measuring device 20. The distance-measuring device 20 is used as a probe to obtain points representative of a surface of the bone, for the CAS processor 1 to define the model of the bone using readings obtained from the distance-measuring device 20. According to an embodiment, the distance-measuring device 20 has an elongated body 21 at the end of which is located receptacle 22 to receive inertial sensor unit 23. In an embodiment, the elongated body 21 is sized so as to be received in the central bore 17 of the spherical joint 16, such that the distance-measuring device 20 is blocked from translating, yet movable in three rotational degrees of freedom because of the spherical joint 16.

The distance-measuring device 20 has a pointer end 24. In an embodiment, the pointer end 24 may be telescopically connected to the elongated body 21, to be displaced along the longitudinal axis of the elongated body 21. An encoder (e.g., standard distance encoder, Hall-effect sensor, etc) may be placed at the telescopic joint so as to measure the length of the pointer end 24. Accordingly, the system 1 may calculate the distance of various points of the bone surface, i.e., the distance between the pointer end 24 and the central bore 17. Moreover, as the orientation of the distance-measuring device 20 is known (i.e., its axis) via the data produced by the inertial sensor unit 23, it is possible to obtain a cloud of points representative of the acetabulum surface, as described below. According to an embodiment, the cloud of points may then be transposed into the coordinate system tracked by the inertial sensor unit 14 on the base 11, as explained below. As another feature, the inertial sensor unit 14 may be used to detect movements of the pelvis during the gathering of points made with the inertial sensor unit 14.

As an alternative embodiment, the pointer end 24 is not telescopically connected to the elongated body 21. Instead, the distance-measuring device 20 is allowed to slide relative to the spherical joint 16, the pair forming a sliding joint. A distance-measuring encoder could be placed at the sliding joint to measure the displacement. Alternatively, the distance could be measured by the inertial sensor unit 23. The distance-measuring device 20 may be an optical rangefinder, connected to the ball member 16A and measuring a distance through light emission. It is also considered to use a simple ruler, with an operator entering the distance value between the point on the surface and the reference position along the distance-measuring axis.

Although a pair of inertial sensor units are shown, i.e., 14 and 23, the apparatus may be provided with additional encoders to determine the orientation of the ball member 16A relative to the base 11, in addition to encoders or a rangefinder providing distance values between a reference point, such as the center of rotation of the ball member 16A, and a point on the surface of the anatomical feature intersecting the distance-measuring axis (e.g., the longitudinal axis of the elongated body 21).

Referring to FIG. 5, an embodiment of the CAS processor 1 is shown in greater detail. The CAS processor 1 may include the following modules as part of a non-transitory computer readable memory having recorded thereon statements and instructions for execution by a computer to carry out a method for modelling a surface of an anatomical feature in computer-assisted surgery in a coordinate system. The coordinate system is virtual and may be updated with signals from the inertial sensor units, such as 14 and 23. The CAS processor 1 may output data via a user interface 40.

A distance module 51 obtains a distance between a reference position and a plurality of points of the surface of the anatomical feature. For example, the distance module 51 calculates a distance using the signals from an encoder of the distance-measuring device 24. According to an embodiment, the reference position is the center of rotation of the spherical joint 16 supporting the distance-measuring device 24, as the center of rotation is fixed relative to the base 11 and hence the anatomical feature, and is therefore conveniently used for trigonometric calculations. Other reference positions may be used, such as any part of the distance-measuring device 24.

An orientation module 52 determines, using signals from the inertial sensor unit 23 and/or encoder signals, an orientation of the distance-measuring axis passing through the reference position and the plurality of points of the surface of the anatomical feature.

A position calculator module 53 calculates a position of each point using the orientation of the axis from the orientation module 52 and the distance for this point from the distance module 51. Hence, the position of a plurality of points is calculated, the reference position being common to each of the plurality of points.

A model generating module 54 generates and outputs, using the signals from the inertial sensor unit(s) 14 and 23, the model of the surface in the coordinate system using the position of the plurality of points. The cloud of points may be enough for a virtual model of the surface to be generated, for example, the acetabulum. The model generating module 54 may also obtain the imaged model M of the surface, to match the position of the plurality of points with the imaged model. This may include obtaining the orientation of the anatomical feature, e.g., the virtual coordinate system from pre-operative planning, as a reference for subsequent navigation. The CAS processor 1 may therefore perform some surface matching to match (a.k.a., register) the model to the actual measured surface or may perform other registration methods as well, and hence obtain other geometrical or outline data, such as the position of other landmarks, without resorting to an existing pre-opereative 3D model. This information is captured by the apparatus 10 and inertial sensors 14 and/or 23, and once completed, the distance-measuring device 24 may be removed along with the bracket 15.

A navigation module 55 produces and outputs, using the signals from the inertial sensor unit(s) 14 and 23, orientation data relating an object such as a tool relative to the surface of the anatomical feature using the model of the surface in the coordinate system, as generated by the model generator module 54. As mentioned below, this may require detaching the inertial sensor unit 23 from the distance-measuring device 20, to connect it to a tool. For example, the navigation module 55 outputs an orientation of a bone-altering tool or an implant positioning tool T relative to the anatomic feature, using a tool guide positioned on the base 11 as a replacement for the bracket 15.

Referring to FIG. 6, a method for modelling a surface of an anatomical feature in computer-assisted surgery in a coordinate system is generally shown at 60, and may be performed by the CAS processor unit 1 using the apparatus 10 described above. According to an example, the method is performed on a pelvis to define a surface of the acetabulum.

According to 61, a distance between a reference position and any point of the surface of the anatomical feature is obtained. 61 may include calculating a distance from an encoder of the distance-measuring device 24. The method may be performed using a center of rotation of the spherical joint 16 as reference position.

According to 62, using signals from inertial sensor unit(s) 14 and 23, an orientation of an axis passing through the reference position and any point of the surface of the anatomical feature is determined.

According to 63, a position of any point is calculated using the orientation of the axis and the distance for the point. 61, 62 and 63 are repeated for a plurality of points on the anatomical feature to be obtained, with the reference position being fixed throughout 61, 62 and 63. According to an embodiment, 61, 62 and 63 may also be performed to create a coordinate system of the anatomical feature, in addition to obtain points of the surface to model. For example, in the case of the pelvis, 61, 62 and 63 may obtain a suitable number of landmarks to define a coordinate system of the pelvis. 61, 62 and 63 may be used to obtain the ASIS, and the pubic tubercle, as one possibility.

According to 64, using the inertial sensor unit(s) 14 and 23, the model of the surface in the coordinate system is generated using the position of the plurality of points. This may include using the points obtained for the known landmarks, to create the coordinate system for the model generated from the cloud of points. 64 may include obtaining an imaged model of the surface, such that generating the model of the surface comprises matching or registering the position of the plurality of points with the imaged model. In such a case, a virtual coordinate system representative of the orientation of the anatomical feature may be obtained with the 3D imaged model.

According to 65, using the signals from the inertial sensor unit(s) 14 and 23, orientation data relating an object relative to the surface of the anatomical feature is output, using the model of the surface in the coordinate system. Outputting the orientation data may include outputting an orientation of a bone-altering tool or an implant positioning tool relative to the anatomic feature. According to an embodiment, the inertial sensor unit 14 is on the base 11, and tools may or may not have the inertial sensor unit 23 thereon, detached from the distance-measuring device 20. For example, the base 11 may use the bracket 15 with spherical joint 16 (and associated encoders) to determine the orientation of the tool T. In an alternative embodiment, the tool T supports the inertial sensor unit 23, and the orientation of the tool T is navigated using the readings of both inertial sensor units 14 and 23.

Therefore, the CAS processor 1 and method 60 may track tools relative to a bone using a single inertial sensor unit (14 or 23) on the base 11 during the navigation, after the modelling or registration has been performed, with the inertial sensor unit 14 and/or 23. The CAS processor 1 uses encoder data and/or geometrical data of its bracket 15 or like attachment guiding the tool T, to determine the orientation in the coordinate system tracked by the inertial sensor unit 14 secured to the base 11. In an embodiment, it is contemplated to use a single inertial sensor unit secured to the distance-measuring device 20 with landmarks being detected on the anatomical feature to create a coordinate system. If the inertial sensor unit is then detached from the distance-measuring device 20 to be positioned onto the base 11 for navigation, some geometric relation must be recorded prior to detaching the inertial sensor unit and tracking same in dead-reckoning, for the acquired cloud of points and coordinate system to be in a known geometric relation relative to the base 11.

While the methods and systems described herein have been described and shown with reference to particular steps performed in a particular order, it will be understood that these steps may be combined, subdivided or reordered to form an equivalent method without departing from the teachings of the present invention. Accordingly, the order and grouping of the steps is not a limitation of the present invention.

The invention claimed is:

1. An apparatus for obtaining points of a surface of an anatomical feature comprising:
a base adapted to be secured to an anatomical feature;

a spherical joint supported by the base, the spherical joint having a ball member rotatable in at least two rotational degrees of freedom relative to the base and having a center of rotation fixed relative to the base;

a distance-measurement device connected to the ball member such that a distance-measurement axis of the distance-measurement device passes through said center of rotation of the ball member, the distance-measurement device configured for providing a distance of any point of the surface intersecting the distance-measurement axis; and at least one receptacle configured to receive an inertial sensor unit for determining an orientation of the distance-measurement device;

whereby a position of any point is obtained using said distance and an orientation of the distance-measurement device as connected to the ball member at a measurement of said any point.

2. The apparatus according to claim 1, wherein the distance-measurement device includes a probe having a body connected to the ball member with a contact end of the body configured to contact the surface of the anatomical feature, the body of the probe connected to the ball member such that the distance-measurement axis is a longitudinal axis of the body passing through said center of rotation of the ball member and said contact end of the body.

3. The apparatus according to claim 2, wherein further comprising a translational joint providing a translation degree of freedom between the contact end of the body of the probe and the center of rotation of the ball member, such that the contact end of the body is configured to come into contact with the surface of the anatomical feature.

4. The apparatus according to claim 2, further comprising an encoder determining a distance between the contact end of the body and the center of rotation of the ball member.

5. The apparatus according to claim 1, wherein the at least one receptacle is on the distance-measurement device.

6. The apparatus according to claim 5, wherein another said receptacle is on the base, such that the apparatus is configured to support said inertial sensor unit on the distance-measurement device, and another inertial sensor unit on the base.

7. The apparatus according to claim 1, further comprising a handle secured to the base for positioning the base against the anatomical feature.

8. The apparatus according to claim 7, wherein the handle concurrently forms a concavity with the base configured for receiving a protuberance of the anatomical feature.

9. The apparatus according to claim 7, wherein the handle is removable from the base once the base is secured to the anatomical feature.

10. The apparatus according to claim 1, wherein the ball member defines a counterbore having an axis coincident with said center of rotation, the counterbore receiving and supporting the distance-measurement device.

11. The apparatus according to claim 1, further comprising a tool guide having a guiding feature configured for receiving a tool altering the anatomic feature.

12. The apparatus according to claim 11, wherein the tool guide is connected to the base after removal of the spherical joint.

* * * * *